United States Patent
Wellner et al.

(10) Patent No.: US 7,339,059 B2
(45) Date of Patent: Mar. 4, 2008

(54) BENZOFURANS AND INDOLS

(75) Inventors: Eric Wellner, Lund (SE); Helena Sandin, Lund (SE)

(73) Assignee: Active Biotech AB, Lund (SE)

( * ) Notice: Subject to any disclaimer, the term of this patent is extended or adjusted under 35 U.S.C. 154(b) by 455 days.

(21) Appl. No.: 10/995,037

(22) Filed: Nov. 23, 2004

(65) Prior Publication Data

US 2005/0192288 A1   Sep. 1, 2005

(30) Foreign Application Priority Data

Feb. 25, 2004   (SE) .................................. 0400441

(51) Int. Cl.
*C07D 405/00* (2006.01)
(52) U.S. Cl. .................................. 544/376
(58) Field of Classification Search ...................... None
See application file for complete search history.

(56) References Cited

U.S. PATENT DOCUMENTS

| | | |
|---|---|---|
| 4,115,569 A | 9/1978 | Weber et al. |
| 4,374,990 A | 2/1983 | Weber et al. |
| 5,814,644 A | 9/1998 | Kulagowksi et al. |

FOREIGN PATENT DOCUMENTS

| | | |
|---|---|---|
| WO | WO 98 56771 A2 | 12/1998 |
| WO | WO 01 49678 A1 | 7/2001 |
| WO | WO 01 64676 A2 | 9/2001 |
| WO | WO 01 72728 A2 | 10/2001 |
| WO | WO 2004 037796 A2 | 5/2004 |

OTHER PUBLICATIONS

West, Anthony R., Solid State Chemistry and Its Applications, Wiley, New York, 1988, 358.*
Salome Younes, et al., Synthesis and Structure-activity Relationship of Novel Arylalkyl 4-benzyl Piperazine Derivatives as O Site Selective Ligands, Eur. J. Med. Chem., 35, 107-121, table II (2000).*
Karpus et al "An Important Role for the Chemokine Macrophage Inflammatory Protein-1α in the Pathogenesis of the T Cell-Mediated Autoimmune Disease, Experimental Autoimmune Encephalomyelitis" J. Immunol (1995) vol. 155, pp. 5003-5010.
Hino et al "2-Hydroxy-1-substituted-1,2,3,4-tetrahydro-β-carbolines. The Pictet-Spengler Reaction of N-Hy-droxytryptamine with Aldehydes" Chem. Pharm. Bull. (1990) vol. 38, pp. 59-64.
Hodges et al "Synthesis and Antineoplastic activity of Mitosene Analogues of the Mitomycins" J. Med. Chem. (1981) vol. 24, pp. 1184-1191.
Horuk, R. et al "A Non-peptide Functional antagonist of the CCR1 Chemokine Receptor Is Effective in Rat Heart Transplant Rejection" J. Biol. Chem (2001) vol. 276, pp. 4199-4204.
Horuk, R. et al "Chemokine Receptor Antagonists" Med. Res. Rev. (2000) vol. 20, pp. 155-168.
Horuk, R. "Development and evaluation of pharmacological agents targeting chemokine receptors" Methods (2003) vol. 29, pp. 369-375.
Salome Younes et al "Synthesis and structure-activity relationship of novel arylalkyl 4-benzyl piperazine derivatives as o site selective ligands" Eur. J. Med. Chem., 35 (2000) pp. 107-121, table II.
Snowden, N. et al "RANTES role in rheumatoid arthritis" Lancet (1994) vol. 343, pp. 547-548.
Tabia et al "2,3-Dihydro-2-oxo-1 H-benzimidazole-1-carboxamides with Selective Affinity for the 5-HT$_4$ Receptor: Synthesis and Structure-Affinity and Structure-Activity Relationships of a New Series of Partial Agonist and Antagonist Derivatives" J. Med. Chem (1999) vol. 42, pp. 2870-2880.
Dale L. Boger et al; "Non-Amide-Based Combinatiorial Libraries Derived from N-Boc-Iminodiacetic Acid: Solution-Phase Synthesis of Piperazinone Libraries with Activity Against LEF-1/beta-Catenin-Medicated Transcription"; Helvetica Chemica Acta; 2000; pp. 1825-1845; vol. 83.

* cited by examiner

*Primary Examiner*—James O. Wilson
*Assistant Examiner*—Erich Leeser
(74) *Attorney, Agent, or Firm*—Browdy and Neimark, PLLC

(57) ABSTRACT

Compounds of formula (I)

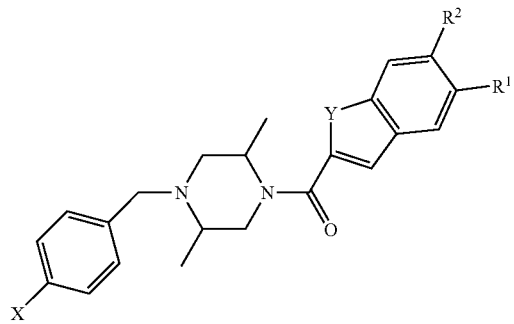

wherein
X is a fluorine or a chlorine atom;
the methyl groups located at the 2- and 5-position of the piperazine ring are in trans-configuration to each other;
Y is NH or O;
$R^1$ is selected from hydrogen, chloro, bromo, nitro, methyl or trifluoromethyl;
$R^2$ is selected from hydrogen, halo, methyl, trifluoromethyl, methoxy or trifluoromethoxy;
or a pharmaceutically acceptable salt or solvate thereof;

The invention also relates to pharmaceutical compositions containing a compound of formula (I) together with a pharmaceutically acceptable carrier. Included are also processes for the preparation of compounds of formula (I), as well as methods for treating mammals suffering from inflammatory, autoimmune, proliferative or hyperproliferative diseases by administering a compound having the formula (I) to said mammal.

3 Claims, No Drawings

BENZOFURANS AND INDOLS

FIELD OF THE INVENTION

This invention relates to novel benzofuran-2-yl-carbonyl- and indol-2-yl-carbonyl-trans-2,5-dimethyl-piperazine derivatives, their pharmaceutically acceptable salts, pharmaceutical compositions containing them and their use in therapy.

Another aspect of the invention is a method of treating inflammatory, autoimmune, proliferative and hyperproliferative diseases. A preferred method is the method of treating rheumatoid arthritis, atherosclerosis, systemic sclerosis, multiple sclerosis, Alzheimer's disease, encephalomyelitis, systemic lupus erythematosus, Guillian-Barre syndrome, allograft rejection, urticaria, angioderma, allergic conjunctivitis, atopic dermatitis, allergic contact dermatitis, drug or insect sting allergy, systemic anaphylaxis, proctitis, inflammatory bowel disease or asthma.

BACKGROUND

Chemokines are small secreted cytokines consisting of 8-14 kDa proteins, which can be classified into four groups according to the sequence of their conserved cysteine residues, CXC, CC, C and $CX_3C$. They promote upregulation of cellular adhesion molecule, which enforces adhesion and lead to cell migration. Hence, the chemotactic cytokines play a crucial part in the recruitment and trafficking of leukocyte subsets.

Among the CC chemokines, MIP-1α and RANTES, known as ligands for CCR1, CCR3, CCR4 and CCR5 receptors, are involved in autoimmune diseases such as rheumatoid arthritis, inflammatory bowel disease and multiple sclerosis. This is strongly supported by the fact that CCR1 knockout mice show a significantly reduced incidence of disease in a mouse EAE model compared with the wild type mice. Studies by Karpus et al (J. Immunol. 1995, 155, 5003) further prove the pivotal role of MIP-1α in the same model of multiple sclerosis. It was shown that antibodies to MIP-1α prevented the development of both acute and relapsing paralytic disease as well as infiltration of mononuclear cells into the CNS.

In addition, there is strong evidence implicating RANTES in the pathophysiology of rheumatoid arthritits. For example, RANTES mRNA was detected in synovial tissue samples from patients with rheumatoid arthritis (Snowden, N. et al., Lancet, 1994, 343, 547). Further, antibodies to RANTES greatly reduced the development of disease in an adjuvant-induced arthritis model in the rat.

A number of studies have provided evidence for a role of CCR1 in allograft rejection. Combining a sub-nephrotoxic amount of cyclosporin A with blockade of chemokine receptors using a CCR1 antagonist has been shown to have a positive effect on solid allograft survival (Horuk, R. et al., J. Biol. Chem. 2001, 276, 4199).

Therefore, molecules that inhibit the interaction between the inflammatory chemokines and their receptor would be beneficial in the treatment of inflammatory, autoimmune, proliferative and hyperproliferative diseases.

RELATED DISCLOSURES

The International Patent Application WO 0164676 claims (cis)-4-(4-fluorobenzyl)-1-(7-methoxy-benzofuran-2-yl-carbonyl)-2,5-dimethylpiperazine as p38 kinase inhibitor.

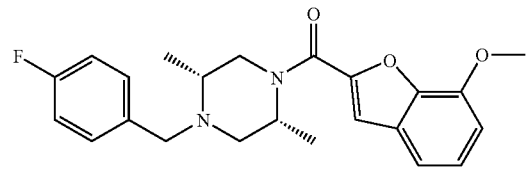

The document is directed to compounds that are useful in treating inflammation and cardiac conditions. More particularly, the document concerns compounds to treat proinflammatory and heart and kidney conditions. No other specific benzofurans are claimed or exemplified.

The U.S. Pat. No. 5,814,644 discloses one indol-2-carbonyl derivative as synthetic building block for the preparation of dopamine antagonists, which are of benefit in the treatment of psychotic disorders.

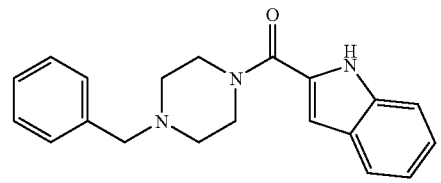

The U.S. Pat. Nos. 4,115,569 and 4,374,990 claim derivatives of piperazine containing substituents of benzofuran as psychotherapeutic drugs.

DESCRIPTION OF THE INVENTION

It has now surprisingly been found that compounds of general formula (I)

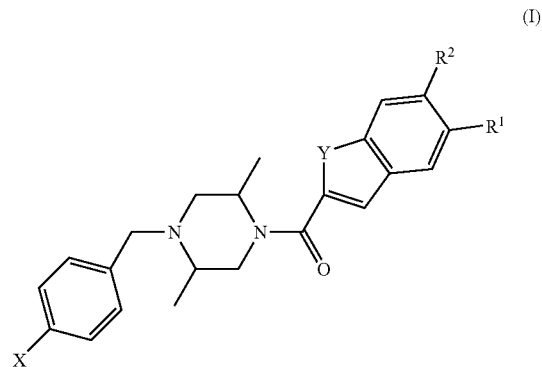

(I)

wherein:
X is a fluorine or a chlorine atom;
the methyl groups located at the 2- and 5-position of the piperazine ring are in trans-configuration to each other;
Y is NH or O;
$R^1$ is selected from hydrogen, chloro, bromo, nitro, methyl or trifluoromethyl;
$R^2$ is selected from hydrogen, halo, methyl, trifluoromethyl, methoxy or trifluoromethoxy;
or a pharmaceutically acceptable salt or solvate thereof;
are unexpectedly effective in inhibiting the signalling of the chemokine receptor CCR1.

Of the compounds of the formula (I) as defined above, a preferred group of compounds of formula (I) is that group of compounds wherein:
X is a fluorine atom;
Y is NH or O;
$R^1$ is selected from hydrogen, chloro or bromo;
$R^2$ is selected front hydrogen, chloro, bromo, methyl, trifluoromethyl, methoxy or trifluoromethoxy.

Among the preferred compounds are:
(trans)-1-(5-Bromo-benzofuran-2-yl-carbonyl)-4-(4-fluorobenzyl)-2,5-dimethylpiperazine
(trans)-4-(4-Chlorobenzyl)-1-(5-chloro-indol-2-yl-carbonyl)-2,5-dimethylpiperazine
(trans)-4-(4-Fluorobenzyl)-1-(6-methyl-benzofuran-2-yl-carbonyl)-2,5-dimethylpiperazine
(trans)-4-(4-Fluorobenzyl)-1-(6-trifluoromethoxy-benzofuran-2-yl-carbonyl)-2,5-dimethylpiperazine
(trans)-1-(5-Chloro-6-methoxy-benzofuran-2-yl-carbonyl)-4-(4-fluorobenzyl)-2,5-dimethylpiperazine
(trans)-1-(5-Bromo-6-methoxy-benzofuran-2-yl-carbonyl)-4-(4-fluorobenzyl)-2,5-dimethylpiperazine
(trans)-1-(5-Chloro-6-methyl-benzofuran-2-yl-carbonyl)-4-(4-fluorobenzyl)-2,5-dimethylpiperazine
(trans)-1-(5-Bromo-6-methyl-benzofuran-2-yl-carbonyl)-4-(4-fluorobenzyl)-2,5-dimethylpiperazine
(trans)-1-(5,6-Dichloro-indol-2-yl-carbonyl)-4-(4-fluorobenzyl)-2,5-dimethylpiperazine
(trans)-1-(6-Bromo-5-chloro-indol-2-yl-carbonyl)-4-(4-fluorobenzyl)-2,5-dimethylpiperazine
(trans)-1-(5-Bromo-6-chloro-indol-2-yl-carbonyl)-4-(4-fluorobenzyl)-2,5-dimethylpiperazine
(trans)-1-(5-Chloro-6-trifluoromethyl-indol-2-yl-carbonyl)-4-(4-fluorobenzyl)-2,5-dimethylpiperazine
(trans)-1-(5-Chloro-benzofuran-2-yl-carbonyl)-4-(4-fluorobenzyl)-2,5-dimethylpiperazine Examples of the preferred compounds of the invention in the above formula (I) are shown in the following Table 1.

TABLE 1

| Compound No. | Structure |
|---|---|
| 3.1 | 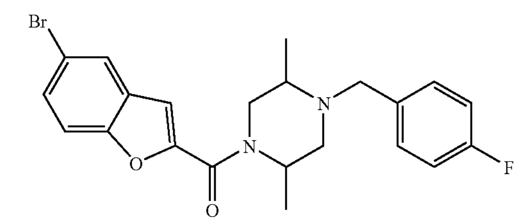 |
| 4.1 | 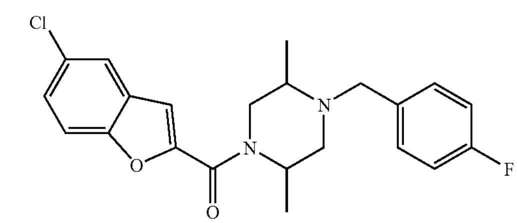 |
| 3.9 | 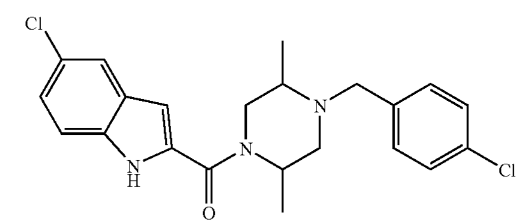 |
| 3.13 | 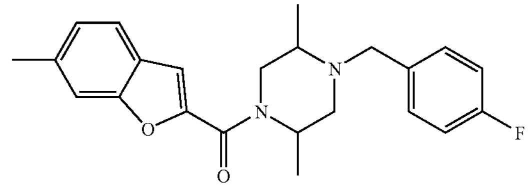 |
| 3.14 | 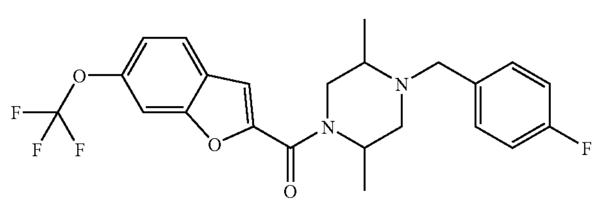 |

TABLE 1-continued

| Compound No. | Structure |
|---|---|
| 3.15 | 5-chloro-6-methoxybenzofuran-2-yl carbonyl-(2,5-dimethylpiperazin-1-yl) with 4-fluorobenzyl on N4 |
| 3.16 | 5-bromo-6-methoxybenzofuran-2-yl carbonyl-(2,5-dimethylpiperazin-1-yl) with 4-fluorobenzyl on N4 |
| 3.18 | 5-chloro-6-methylbenzofuran-2-yl carbonyl-(2,5-dimethylpiperazin-1-yl) with 4-fluorobenzyl on N4 |
| 3.19 | 5-bromo-6-methylbenzofuran-2-yl carbonyl-(2,5-dimethylpiperazin-1-yl) with 4-fluorobenzyl on N4 |
| 3.20 | 5,6-dichloro-1H-indol-2-yl carbonyl-(2,5-dimethylpiperazin-1-yl) with 4-fluorobenzyl on N4 |
| 3.21 | 5-chloro-6-bromo-1H-indol-2-yl carbonyl-(2,5-dimethylpiperazin-1-yl) with 4-fluorobenzyl on N4 |
| 3.22 | 5-bromo-6-chloro-1H-indol-2-yl carbonyl-(2,5-dimethylpiperazin-1-yl) with 4-fluorobenzyl on N4 |

TABLE 1-continued

| Compound No. | Structure |
|---|---|
| 3.23 | 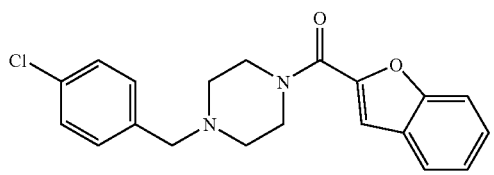 |

Definitions

The term "therapy" and "treatment" as used herein includes prophylaxis as well as relieving the symptoms of disease.

Unless specified otherwise:

"Halo" or "halogen" refers to fluoro, chloro, bromo or iodo.

"Nitro" refers to the radical —$NO_2$.

$CHCl_3$ refers to chloroform.

$CH_2Cl_2$ refers to dichloromethane.

The descriptor "trans" indicates that the two methyl groups are located on opposite sides of the piperazine plane. The descriptor "cis" indicates that the two methyl groups are located at the same side of the piperazine plane.

Structure Activity Relationship

Prior art and Reference Compounds (cis)-4-(4-Fluorobenzyl)-1-(7-methoxy-benzofuran-2-yl-carbonyl)-2,5-dimethylpiperazine, 4-(4-fluorobenzyl)-1-(indol-2-yl-carbonyl)-piperazine, 4-(4-chlorobenzyl)-1-(benzofuran-2-yl-carbonyl)-piperazine and (trans)-4-(4-fluorobenzyl)-1-(7-methoxy-benzofuran-2-yl-carbonyl)-2,5-dimethylpiperazine are included as prior art and reference compounds hereinafter called Compound A, B, C and D respectively. Compound A is described in the International Patent Application WO 0164676. Compound C is described in U.S. Pat. No. 4,115,569. Compound B and D are reference compounds, not according to the invention.

Compound A

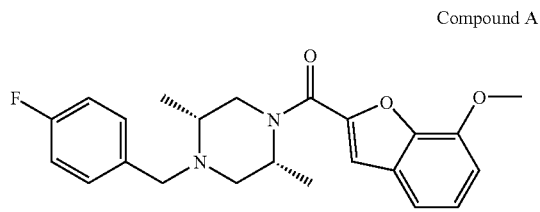

Compound B

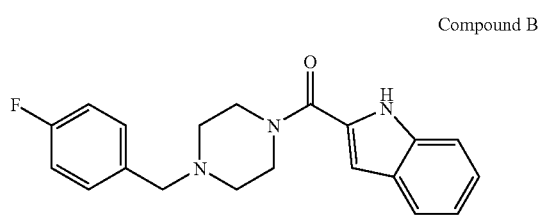

Compound C

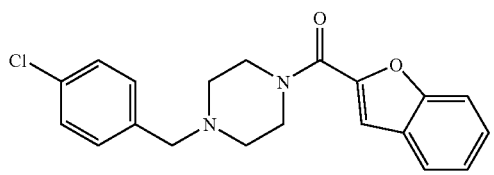

Compound D

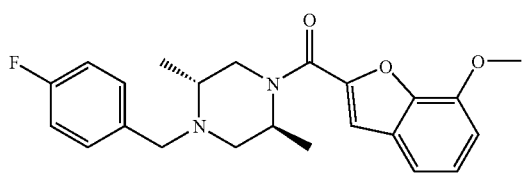

Compared to the prior art Compounds A, and C and reference Compounds B and D, the compounds of the invention were much stronger inhibitors in the $Ca^{2+}$-flux assay. The improved potency of the compounds correlates amongst others to the following structural features.

1. The introduction of chloro or preferably fluoro in p-position of the benzylpiperazine moiety is crucial to gait activity in the nano molar range of the $Ca^{2+}$-flux assay. The replacement of X with another functional group, e.g., alkyl, or hydrogen decreases the potency and the affinity.
2. The two methyl groups in 2,5-position are in trans-configuration. The replacement of the methyl groups in trans-2,5-position by a substitution with hydrogen as well as changing the orientation to a cis-2,5 substitution, dramatically decreases the potency of the compounds in the $Ca^{2+}$-flux assay.
3. $R^1$ has to be a group with a molrefractory (MR) value of $5.0 \leq MR \leq 9.0$, such as chloro, bromo, methyl, nitro or trifluoromethyl.
4. The 4- and 7-position of the benzofuran and indole ring systems must not be substituted.

The invention, combining the features according to 1, 2, 3 and 4 above, provides compounds having a surprising and unexpected potency (see Table 2).

The compounds of the invention showed favourable pharmacokinetic properties.

A definition of the MR conception and the values thereof are available in the following two references:

Hansch, C., and Leo, A., In Exploring QSAR: Fundamentals and Applications in Chemistry and Biology. ACS, Washington, D.C. 1995.

Hansch, C., Leo, A., and Hoekman, D., In Exploring QSAR: Hydrophobic, Electronic, and Steric Constants. ACS, Washington, D.C. 1995.

Preparation of Compounds

The present invention further provides a process for the preparation of a compound of formula (I) by the method given below.

Method:

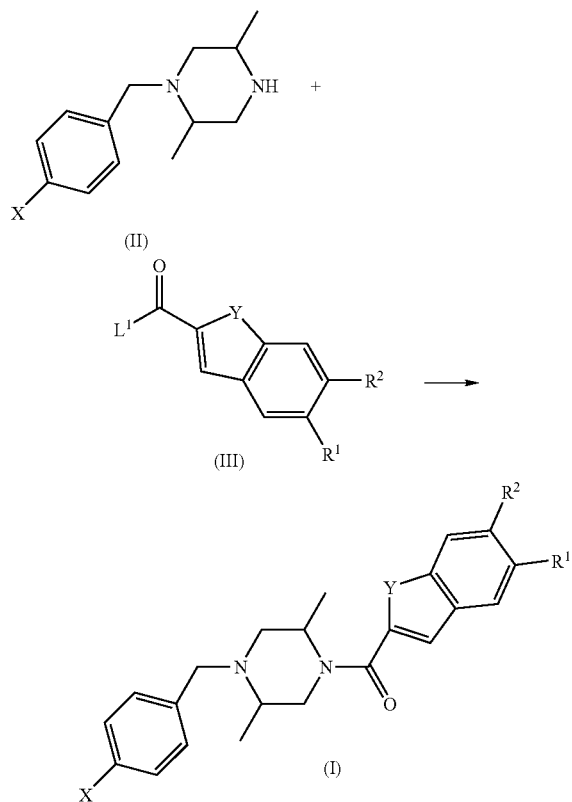

The compounds of formula (I) may be prepared by treating the piperazine derivative of formula (II), wherein X is defined in formula (I), with a compound of formula (III), wherein $L^1$ is a leaving group (e.g. a halide such as chloride, a hydroxyl, a benzotriazol-1-yl ester, an isourea group) and Y, $R^1$ and $R^2$ are defined in formula (I). The process of the invention may conveniently be carried out in $CH_2Cl_2$ or $CHCl_3$ at a temperature of, for example, 0° C. or above such as 20 to 120° C.

Most preferred is a process where the amine derivative of formula (II) in chloroform is treated with an excess molar amount of a compound of formula (III), wherein $L^1$ is a hydroxy group, in the presence of an excess molar amount of a carbodiimde, such as N-cyclohexyl-carbodiimide, N'-methylpolystyrene, and 1-hydroxybenzotriazol. The reaction mixture is stirred at a temperature typically in the range from 60° C. to 150° C. under a time typically in the range from 100 to 1000 seconds in a microwave oven (Smith Synthesiser from Personal Chemistry). Under these conditions the yields improve up to 99%. Compounds of formula (I) may be obtained via a known protocol described e.g., in Tabia et al., J. Med. Chem. 1999, 42, 2870. Compounds falling within the scope of formula (II) may be prepared by methods, which are generally analogous to those of said literature. Compounds of the formula (III) are commercially available or are described in Example 1, Example 2, and Example 4. Compounds falling within the scope of formula (III) may be prepared by methods, which are generally analogous to those of said literature (Hodeges et al., J. Med. Chem. 1981, 24, 1184; Hino et al., Chem. Pharm. Bull. 1990, 38, 59) or according to Example 1, Example 2, and Example 4.

The present invention can also use acidic adducts of the dimethyl-piperazine derivatives with acids including for example hydrochloric acid, hydrobromic acid, hydroiodic acid, sulfuric acid, phosphoric acid, carbonic acid, malic acid, citric acid, fumaric acid, tartaric acid, oxalic acid, methanesulfonic acid, p-toluenesulfonic acid, trifluoroacetic acid and others. Lists of additional suitable salts are found in Remington's Pharmaceutical Sciences, 17th edition, Mack Publishing Company, Easton, Pa., 1985, p. 1418.

EXAMPLE 1

5-Bromo-1-benzofuran-2-carboxylic Acid

To a solution of 5-bromosalicyaldehyde (20 g, 98.5 mmol) and diethyl bromomalonate (95%, 37 g, 148 mmol) in butanone (200 mL) potassium carbonate (27.5 g, 197 mmol) was added. The mixture was refluxed for 4 h and allowed to attain room temperature Potassium carbonate was filtered off and the solvent was removed in vacuo. The residue was participated between $CH_2Cl_2$ and 1M aqueous $H_2SO_4$. The organic layer was dried and concentrated to give an oil. The oil was treated with 10% KOA/EtOH (125 mL) and refluxed for 45 minutes. The reaction mixture was concentrated and 2M aqueous $H_2SO_4$ (350 mL) was added and the mixture was warmed to 90° C. After cooling to room temperature, the product precipitated and was re-crystallised in $EtOH/H_2O$ (4:1) (yield: 6.6 g, 28%).

$^1$H NMR: δ(DMSO-$d_6$) 13.55 (bs, 1H), 7.97 (d, 1H), 7.67 (d, 1H), 7.60 (m, 2H).

Other 1-benzofuran-2-carboxylic acid can be obtained in a similar manner.

EXAMPLE 2

5,6-Dichloro-1-indole-2-carboxylic Acid

To an ice-cooled mixture of 3,4-dichlorotoluene (10.0 g, 62.1 mmol) and sulfuric acid (96-98%, 50 mL) nitric acid (100%, 2.87 mL, 68.3 mmol) was added dropwise under vigorous stirring at such a rate that the reaction temperature did not exceed 15° C. After the addition the reaction mixture was allowed to reach room temperature and was stirred for an additional 60 minutes. The reaction mixture was poured onto 250 mL of ice and the precipitated product was isolated by filtration with suction, washed with water, dried under vacuum and finally re-crystallized from heptane (yield of 4,5-dichloro-2-nitrotoluene: 4.4 g, 34%).

$^1$H NMR: δ($CDCl_3$) 8.10 (s, 1H); 7.65 (s, 1H); 2.57 (s, 3H).

To a solution of 4,5-dichloro-2-nitrotoluene (2.0 g, 9.7 mmol) in $CCl_4$ (15 mL) was added N-bromosuccinimide (2.6 g, 15 mmol) and $Bz_2O_2$ (50 mg). The reaction mixture was refluxed for 120 hours and then allowed to reach room temperature. The reaction mixture was washed twice with water, dried and concentrated to yield 3.54 g of a crude product consisting of approximately 70% of 4,5-dichloro-2-nitrobenzyl bromide and 30% of 4,5-dichloro-2-nitrobenzyl dibromide. This mixture was suspended in a mixture of 1,4-dioxane (35 mL) and water (35 mL). CaCO₃ (6.2 g, 62 mmol) was added and the reaction mixture was refluxed for 18 hours. The reaction mixture was allowed to reach room temperature and was then concentrated to dryness. To a suspension of the remainder in CH₂Cl₂ (50 mL) was adde 2M aqueous HCl until no solid remained. The aqueous layer was extracted with CH₂Cl₂ and the combined organic layer was dried and concentrated. The crude product was dissolved in toluene and purified by flash chromatography using silica gel 60 and heptane/ethyl acetate (19:1→4:1) (yield of 4,5-dichloro-2-nitrobenzyl alcohol: 1.15 g, 53%).

¹H NMR: δ(CDCl₃) 8.27 (s, 1H); 7.98 (s, 1H); 5.02 (s, 2H).

To a solution of 4,5-dichloro-2-nitrobenzyl alcohol (1.15 g, 5.2 mmol) in CHCl₃ (20 mL) was added MnO₂ (4.0 g, 47 mmol). The reaction mixture was refluxed for 18 hours and then allowed to reach room temperature. The reaction mixture was filtered through Celite and concentrated (yield of 4,5-dichloro-2-nitrobenzaldehyde: 1.0 g, 87%).

¹H NMR: δ(CDCl₃) 10.20 (s, 1H); 8.07 (s, 1H); 7.84 (s, 1H).

A solution of 4,5-dichloro-2-nitrobenzaldehyde (0.85 g, 3.85 mmol) and (carbethoxymethylene)-triphenylphosphorane (1.84 g, 5.55 mmol) in benzene (25 mL) was refluxed for three hours. The reaction mixture was allowed to reach room temperature and was then concentrated. The crude product was purified by flash chromatography using silica gel 60 and toluene (yield of ethyl(cis,trans)-4,5-dichloro-2-nitro cinnamate: 1.01 g, 90%).

Ethyl(cis,trans)-4,5-dichloro-2-nitro cinnamate (1.01 g, 3.48 mmol) was dissolved in triethyl phosphite (2 mL). The solution was added dropwise to triethyl phosphite (5 mL) at 125° C. After the addition the temperature was raised to 145° C. and the reaction mixture was left at this temperature for two hours. The reaction mixture was allowed to reach room temperature and was then concentrated. The crude product was purified by flash chromatography using silica gel 60 and heptane/toluene (10:1→5:1→1:1→0:1) (yield of ethyl 5,6-dichloroindole-2-carboxylate: 0.18 g, 20%).

¹H NMR: δ(CDCl₃) 8.90 (bs, 1H); 7.81 (s, 1H); 7.57 (s, 1H); 7.16 (s, 1H); 4.48 (q, 2H); 1.45 (t, 3H).

To a solution of ethyl 5,6-dichloroindole-2-carboxylate (0.16 g, 0.64 mmol) in ethanol (99%, 5 mL) was added 1M aqueous NaOH (5 mL). The reaction mixture was refluxed for five minutes and was then allowed to reach room temperature. The ethanol was removed by evaporation and the aqueous residue was acidified using 1M aqueous HCl. The precipitated product was collected by filtration, washed with water and dried under vacuum (yield of 5,6-dichloroindole-2-carboxylic acid: 0.14 g, 96%)

¹H NMR: δ(DMSO-d₆) 13.26 (bs, 1H); 12.06 (s, 1H); 7.94 (s, 1H); 7.60 (s, 1H); 7.07 (d, 1H).

Other indole-2-carboxylic acid can be obtained in a similar manner.

EXAMPLE 3

3.1 (trans)-1-(5-Bromo-benzofuran-2-yl-carbonyl)-4-(4-fluorobenzyl)-2,5-dimethylpiperazine A mixture of (trans)-1-(4-fluorobenzyl)-2,5-dimethylpiperazine (220 mg, 1.0 mmol), 5-bromo-1-benzofuran-2-carboxylic acid (342 mg, 1.5 mmol), 1-hydroxybenzotriazol (200 mg, 1.5 mmol) and N-cyclohexylcarbodiimide, N'-methylpolystyrene (167 g, 3.0 mmol of the resin with a loading of 1.8 mmol/g) in CHCl₃ was heated under 5 minutes at 110° C. in a microwave oven The mixture was allowed to attain room temperature. TBD-methyl polystyrene (1000 mg, 3 mmol of the resin with a loading of 2.9 mmol/g) was added and the mixture was agitated over night. Both resins were filtered off and washed with CHCl₃ and EtOAc. The filtrate was concentrated in vacuo and the residue was submitted to flash column chromatography (toluene→toluene: EtOAc, 20:1→toluene: EtOAc, 1:1) to give the title product in 93% yield.

¹H NMR: δ(CDCl₃) 7.78 (d, 1H), 7.48 (dd, 1H), 7.38 (d, 1H), 7.33 (dd, 2H), 7.19 (s, 1H), 7.01 (dd, 2H), 4.63 (bs, 1H), 4.14 (bs, 1H), 3.62 (m, 2H), 3.46 (d, 1H), 3.08 (bs, 1H), 2.79 (dd, 1H), 2.30 (d, 1H), 1.43 (d, 3H), 1.06 (d, 3H).

The following compounds were prepared in a similar manner:

3.2 (trans)-1-(5-Chloro-benzofuran-2-yl-carbonyl)-4-(4-chlorobenzyl)-2,5-dimethylpiperazine ¹H NMR: δ(CDCl₃) 7.62 (d, 1H), 7.43 (d, 1H), 7.33 (m, 1H), 7.29 (m, 4H), 7.19 (d, 1H), 4.63 (bs, 1H), 4.14 (bs, 1H), 3.54 (m, 3H), 3.08 (bs, 1H), 2.80 (dd, 1H), 229 (d, 1H), 1.43 (d, 3H), 1.06 (d, 3H).

3.3 (trans)-4-(4-Fluorobenzyl)-1-(5-nitro-indol-2-yl-carbonyl)-Z 5-dimethylpiperazine ¹H NMR: δ(CDCl₃) 9.67 (s, 1H), 8.65 (s, 1H), 8.20 (d, 1H), 7.49 (d, 1H), 7.35 (dd, 2H), 7.04 (dd, 2H), 6.92 (s, 1H), 4.81 (m, 1H), 4.33 (d, 1H), 3.57 (m, 3H), 3.15 (bs, 1H), 2.82 (dd, 1H), 2.35 (d, 1H), 1.51 (d, 3H), 1.07 (d, 3H).

3.4 (trans)-4-(4-Fluorobenzyl)-1-(5-nitro-benzofuran-2-yl-carbonyl)-2,5-dimethylpiperazine ¹H NMR: δ(CDCl₃) 8.60 (d, 1H), 8.32 (dd, 1H), 7.61 (d, 1H), 7.34 (m, 3H), 7.02 (dd, 2H), 4.61 (bs, 1H), 4.15 (bs, 1H), 3.56 (in, 3H), 3.11 (bs, 1H), 2.82 (dd, 1H), 2.33 (d, 1H), 1.46 (d, 3H), 1.08 (d, 3H).

3.5 (trans)-4-(4-Fluorobenzyl)-1-(7-methoxy-benzofuran-2-yl-carbonyl)-2,5-dimethylpiperazine (reference compound D)

¹H NMR: δ(CDCl₃) 7.34 (dd, 2H), 7.27 (s, 1H), 7.20 (m, 2H), 7.01 (dd, 2H), 6.87 (dd, 1H), 4.69 (bs, 1H), 4.20 (bs, 1H), 3.99 (s, 314), 3.62 (m, 2H), 3.46 (d, 1H), 3.07 (bs, 1H), 2.80 (dd, 1H), 2.30 (d, 1H), 1.43 (d, 3H), 1.07 (d, 3H).

3.6 (trans)-1-(5-Bromo-indol-2-yl-carbonyl)-4-(4-fluorobenzyl)-2,5-dimethylpiperazine ¹H NMR: δ(CDCl₃) 10.17 (s, 1H), 7.77 (s, 1H), 7.36 (m, 4H), 7.04 (dd, 2H), 6.70 (d, 1H), 4.86 (m, 1H), 4.38 (d, 1H), 3.56 (m, 3H), 3.13 (bs, 1H), 2.81 (dd, 1H), 2.33 (d, 1H), 1.49 (d, 3H), 1.05 (d, 3H).

3,7 (trans)-4-(4-Fluorobenzyl)-1-(5-methyl-indol-2-yl-carbonyl)-2,5-dim ethylpiperazine ¹H NMR: δ(CDCl₃) 9.54 (s, 1H), 7.43 (s, 1H), 7.36 (m, 3H), 7.12 (d, 1H), 7.04 (dd, 2H), 6.70 (d, 1H), 4.88 (m, 1H), 4.40 (d, 1H), 3.56 (m, 3H), 3.12 (bs, 1H), 2.81 (dd, 1H), 2.46 (s, 3H), 2.32 (d, 1H), 1.49 (d, 3H), 1.06 (d, 3H).

3.8 (trans)-1-(5-Chloro-indol-2-yl-carbonyl)-4-(4-fluorobenzyl)-2,5-dimethylpiperazine ¹H NMR δ (CDCl₃) 9.40 (s, 1H); 7.61 (d, 1H); 7.36 (d, 1H); 7.34 (dd, 2H); 7.23 (dd, 1H); 7.03 (m, 2H); 6.69 (d, 1H); 4.82 (m, 1H); 434 (d, 1H); 3.56 (m, 3H); 3.12 (m, 1H); 2.80 (dd, 1H); 2.32 (dd, 1H); 1.48 (d, 3H); 1.05 (d, 3H)

3.9 (trans)-4-(4-Chlorobenzyl)-1-(5-chloro-indol-2-yl-carbonyl)-2,5-dimethylpiperazine $^1$H NMR δ (CDCl$_3$) 9.35 (s, 1H); 7.61 (d, 1H); 7.35 (d, 1H); 7.32 (dd, 4H); 7.23 (dd, 1H); 6.69 (d, 1H); 4.81 (m, 1H); 4.34 (d, 1H); 3.56 (m, 3H); 3.12 (m, 1H); 2.80 (dd, 1H); 2.32 (dd, 1H); 1.48 (d, 3H); 1.05 (d 3H).

3.10 (trans)-4-(4-Chlorobenzyl)-1-(5-nitro-benzofuran-2-yl-carbonyl)-2,5-dimethylpiperazine $^1$H NMR δ (CDCl$_3$) 8.60 (d, 1H); 8.33 (dd, 1H); 7.62 (d, 1H); 7.36 (d, 1H); 7.31 (dd, 4H); 4.61 (m, 1H); 4.12 (m, 1H); 3.56 (m, 3H); 3.11 (m, 1H); 2.82 (dd, 1H); 2.32 (dd, 1H); 1.46 (d, 3H); 1.08 (d, 3H).

3.11 (trans)-1-(5-Bromo-benzofuran-2-yl-carbonyl)-4-(4-chlorobenzyl)-2,5-dimethylpiperazine $^1$H NMR δ (CDCl$_3$) 7.79 (d, 1H); 7.49 (dd, 1H); 7.39 (d, 1H); 7.31 (dd, 4H); 7.20 (d, 1H); 4.63 (m, 1H); 4.14 (m, 1H); 3.55 (m, 3H); 3.09 (m, 1H); 2.80 (dd, 1H); 2.30 (d, 1H); 1.44 (d, 3H); 1.07 (d, 3H).

3.12 (trans)-4-(4-Fluorobenzyl)-1-(5-methyl-benzofuran-2-yl-carbonyl)-2,5-dimethylpiperazine $^1$H NMR δ (CDCl$_3$) 7.51 (d, 1H); 7.34 (dd, 2H); 7.31 (s, 1H); 7.23 (d, 1H); 7.12 (d, 1H); 7.02 (t, 2H); 4.67 (bs, 1H), 4.21 (bd, 1H); 363 (d, 1H); 3.58 (bs, 1H); 3.46 (d, 1H); 3.08 (bs, 1H); 2.80 (dd, 1H); 2.49 (s, 3H); 2.29 (d, 1H); 1.43 (d, 3H); 1.07 (d, 3H).

3.13 (trans)-4-(4-Fluorobenzyl)-1-(6-methyl-benzofuran-2-yl-carbonyl)-2,5-dimethylpiperazine $^1$H NMR δ (CDCl$_3$) 7.42 (s, 1H); 7.38 (d, 1H); 7.34 (dd, 2H); 7.20 (m 2H); 7.02 (t, 2H); 4.68 (bs, 1H); 4.20 (bd, 1H); 3.63 (d, 1H); 3.59 (bs, 1H); 3.51 (d, 1H); 3.08 (bs, 1H); 2.79 (dd, 1H); 2.32 (s, 3H); 2.29 (d, 1H); 1.43 (d, 3H); 1.06 (d, 3H).

3.14 (trans)-4-(4-Fluorobenzyl)-1-(6-trifluoromethoxy-benzofuran-2-yl-carbonyl)-2,5-dimethylpiperazine $^1$H NMR δ (CDCl$_3$) 7.51 (m, 2H); 7.28 (dd, 2H); 7.25 (m, 2H); 7.02 (t, 2H); 5.23 (bs, 1H); 4.15 (bs, 1H); 3.63 (d, 1H); 3.58 (bs, 1H); 3.47 (d, 1H); 309 (bs, 1H); 2.80 (dd, 1H); 2.31 (d, 1H); 1.44 (d, 3H); 1.07 (d, 3H).

3.15 (trans)-1-(5-Chloro-6-methoxy-benzofuran-2-yl-carbonyl)-4-(4-fluorobenzyl)-2,5-dimethylpiperazine $^1$H NMR δ (CDCl$_3$) 7.63 (s, 1H); 7.34 (dd, 2H); 7.17 (s, 1H); 7.06 (s, 1H); 7.00 (t, 2H); 4.66 (bs, 1H); 4.19 (bd, 1H); 3.95 (s, 3H); 3.63 (d, 1H); 3.59 (bd, 1H); 3.47 (d, 1H); 3.08 (bs, 1H); 2.80 (dd, 1H); 2.30 (d, 1H); 1.43 (d, 3H); 1.07 (d, 3H).

3.16 (trans)-1-(5-Bromo-6-methoxy-benzofuran-2-yl-carbonyl)-4-(4-fluorobenzyl)-2,5-dimethylpiperazine $^1$H NMR δ (CDCl$_3$) 7.81 (s, 1H); 7.34 (dd, 2H); 7.16 (s, 1H); 7.04 (s, 1H); 7.02 (t, 2H); 4.65 (bs, 1H), 4.19 (bd, 1H); 3.95 (s, 3H); 3.62 (d, 1H); 3.58 (bd, 1H); 3.47 (d, 1H); 3.08 (bs, 1H); 2.80 (dd, 1H); 2.30 (d, 1H); 1.43 (d, 3H); 1.07 (d, 3H).

3.17 (trans)-4-(4-Fluorobenzyl)-1-(6-methoxy-5-nitro-benzofuran-2-yl-carbonyl)-2,5-dimethylpiperazine $^1$H NMR δ (CDCl$_3$) 8.17 (s, 1H); 7.34 (dd, 2H); 7.24 (s, 1H); 7.17 (s, 1H); 7.02 (t, 2H); 4.62 (bs, 1H), 4.13 (bs, 1H); 3.63 (d, 1H); 3.59 (bs, 1H); 3.47 (d, 1H); 3.10 (bs, 1H); 2.80 (dd, 1H); 2.32 (d, 1H); 1.44 (d, 3H); 1.07 (d, 3H).

3.18 (trans) 1-(5-Chloro-6-methyl-benzofuran-2-yl-car bonyl)-4-(4-fluorobenzyl)-2,5-dimethylpiperazine $^1$H NMR δ (CDCl$_3$) 7.62 (s, 1H); 7.38 (s, 1H); 7.34 (dd, 2H); 7.17 (s, 1H); 7.00 (t, 2H); 4.63 (bs, 1H); 4.16 (bs, 1H); 3.63 (d, 1H); 3.58 (bd, 1H); 3.46 (d, 1H); 3.08 (bs, 1H); 2.79 (dd, 1H); 2.49 (s, 3H); 2.30 (d, 1H); 143 (d, 3H); 1.06 (d, 3H).

3.19 (trans)-1-(5-Bromo-6-methyl-benzofuran-2-yl-carbonyl)-4-(4-fluorobenzyl)-2,5-dimethylpiperazine $^1$H NMR δ (CDCl$_3$) 7.82 (s, 1H); 7.40 (s, 1H); 7.34 (dd, 2H); 7.16 (s, 1H); 7.02 (t, 2H); 4.63 (bs, 1H); 4.15 (bs, 1H); 3.62 (d, 1H); 3.59 (bs, 1H); 3.46 (d, 1H); 3.08 (bs, 1H); 2.79 (dd, 1H); 2.51 (s, 3H); 2.29 (d, 1H); 1.43 (d, 3H); 1.06 (d, 3H).

3.20 (trans)-(5,6-Dichloro-indol-2-yl-carbonyl)-4-(4-fluorobenzyl)-2,5-dimethylpiperazine $^1$H NMR δ (CDCl$_3$) 9.31 (bs, 1H); 7.72 (s, 1H); 7.54 (s, 1H); 7.34 (dd, 2H); 7.03 (t, 2H); 6.67 (d, 1H); 4.79 (bs, 1H); 4.31 (bd, 1H); 3.63 (d, 1H); 3.58 (bs, 1H); 3.47 (d, 1H); 3.12 (bs, 1H); 2.79 (dd, 1H); 2.32 (d, 1H); 1.47 (d, 3H), 1.05 (d, 3H).

3.21 (trans)-1-(6-Bromo-5-chloro-indol-2-yl-carbonyl)-4-(4-fluorobenzyl)-2,5-dimethylpiperazine $^1$H NMR δ (CDCl$_3$) 9.38 (bs, 1H); 7.13 (s, 1H); 7.72 (s, 1H); 7.34 (dd, 2H); 7.03 (t, 2H); 6.66 (d, 1H); 4.78 (bs, 1H); 4.31 (bd, 1H); 3.63 (d, 1H); 3.58 (bs, 1H); 3.47 (d, 1H); 3.12 (bs, 1H); 2.79 (dd, 1H); 2.32 (d, 1H); 1.47 (d, 3H), 1.05 (d, 3H).

3.22 (trans)-1-(5-Bromo-6-chloro-indol-2-yl-carbonyl)-4-(4-fluorobenzyl)-2,5-dimethylpiperazine $^1$H NMR δ (CDCl$_3$) 9.60 (bs, 1H); 7.89 (s, 1H); 7.57 (s, 1H); 7.35 (dd, 2H); 7.03 (t, 2H); 6.66 (s, 1H); 479 (bs, 1H); 4.32 (bd, 1H); 3.63 (d, 1H); 3.59 (bs, 1H); 3.47 (d, 1H); 3.12 (bs, 1H); 2.80 (dd, 1H); 2.33 (d, 1H); 1.47 (d, 3H), 1.05 (d, 3H).

3.23 (trans)-1-(5-chloro-6-trifuoromethyl-indol-2-yl-carbonyl)-4-(4-fluorobenzyl)-2,5-dimethylpiperazine $^1$H NMR δ (CDCl$_3$) 9.93 (bs, 1H); 7.82 (s, 1H); 7.75 (s, 1H); 7.35 (dd, 2H); 7.03 (t, 2H); 6.72 (d, 1H); 4.80 (bs, 1H); 4.33 (bd, 1H), 3.67 (bs, 1H); 3.64 (d, 1H); 3.48 (d, 1H); 3.13 (bs, 1H); 2.81 (dd, 1H); 2.34 (d, 1H); 1.49 (d; 3H); 1.05 (d, 3H).

EXAMPLE 4

4.1 (trans)-1-(5-Chloro-benzofuran-2-yl-carbonyl)-4-(4-fluorobenzyl)-2,5-dimethylpiperazine A solution of 5-chloro-1-benzofuran-2-carboxylic acid (827 mg, 42 mmol) in thionyl chloride (4 mL) was refluxed over night. The solvent was removed in vacuo to give the 5-chloro-1-benzofuran-2-carbonyl chloride in quantitative yield.

To an ice cold solution of (trans)-1-(4-fluorobenzyl)-2,5-dimethylpiperazine (712 mg, 3.2 mmol) and triethylamine (506 mg, 5 mmol) in CH$_2$Cl$_2$ (5 mL) a solution of the 5-chloro-1-benzofuran-2-carbonyl chloride (4.2 mmol) in CH$_2$Cl$_2$ (2 mL) was dropwise added. The reaction mixture was stirred at room temperature over night and washed with 0.5 M aqueous NaOH. The organic layer was dried, concentrated and submitted to flash column chromatography (CHCl$_3$/MeOH; 1:0→10:1) to yield 1.05 g (82%) of the title compound.

$^1$H NMR: δ(CDCl$_3$) 7.59 (d, 1H), 7.40 (d, 1H), 7.31 (m, 3H), 7.17 (d, 1H), 6,99 (dd, 2H), 4.61 (bs, 1H), 4.12 (bs, 1H), 3.60 (m, 2H), 3.44 (d, 1H), 3.06 (bs, 1H), 2.77 (dd, 1H), 2.28 (d, 1H), 1.41 (d, 3H), 1.04 (d, 3H).

Pharmacological Methods

In Vitro Assay

In the competitive affinity binding assay, the binding affinity of the compounds for the CCR1 receptor can be determined by measuring their ability to displace $^{125}$I-Mip-1α from the CCR1 receptor.

The binding of Mip-1α at the CCR1 receptor leads to an increase of intracellular calcium levels. The ability of the compounds of the invention to block this biologic response of the CCR1 receptor is determined in the Ca$^{2+}$-flux assay.

In Vitro Competitive Affinity Binding Assay

Reagents and Solutions:
1. Screen Ready™ Targets: cloned human CCR1 Chemokine receptor, expressed in CHO cells, coated on 96-well FlashPlate® (Perkin Elmer Cat #6120525)
2. Ligand: $^{125}$I-MIP-1α from Perkin Elmer (specific activity is 2200 Ci/mmol) was reconstituted to 25 μCi/mL in H$_2$O.
3. Assay buffer: 50 mM HEPES, 1 mM CaCl$_2$, 5 mM MgCl$_2$, 0.2% BSA, pH 7.4.
4. MIP-1α (Peprotech EC Ltd Cat # 300-08)
5. The compounds of the invention were dissolved in DMSO. A serial dilution was made and ten concentrations of each compound were screened to generate a dose curve from which the IC$_{50}$ value was determined.

Assay Procedure:

Membranes coated on the FlashPlate® were incubated with $^{125}$I-MIP-1α in the presence and absence of different concentrations of compounds at ambient temperature for 1 hour. The radioactivity in each well was determined in a microplate scintillation counter. The non-specific binding was defined by binding in the presence of 1250-fold unlabeled MIP-1α. The assay was performed according to the manufacturer's instruction of Screen Ready™ Targets. The compounds of the invention, when tested in this assay, demonstrated affinity to the CCR1 receptor.

In Vitro Ca$^{2+}$-Flux Assay on Human Monocytes

Reagents and Solutions:
1. Cell Culture:
   a) THP-1 (ATCC Cat# TIB202)
   b) Tissue culture medium: RPMI 1640 with Ultraglutamine 1 supplemented with 10% (v/v) foetal calf serum. This medium is hereinafter referred to as "growth medium".
2. Assay buffer: HBSS (Hanks' balanced salts solution), 20 mM HEPES, 1 mM CaCl$_2$, 1 mM MgCl$_2$, 2.5 mM Probenecid, pH 7.4.
3. Fluo-4AM (Molecular Probes Cat # F14201)
4. Pluronic® F-127 (Molecular Probes Cat # P-6867)
5. The compounds of the invention were dissolved in DMSO. A serial dilution was made and nine concentrations of each compound were screened to generate a dose curve from which the IC$_{50}$ value was determined.
6. MIP-1α (Peprotech EC Ltd Cat# 300-08)
7. Victor$^2$ 1420 (Perkin Elmer)
8. Microlite™$^{2+}$ (Dynex Cat # 7572)

Assay Procedure:

THP-1 cells were grown in T-75 cm$^2$ flasks in growth medium at 37° C. in 5% CO$_2$. The cells were harvested by centrifugation and resuspended in assay buffer. The cells were then loaded with 5 μM Fluo-4 and 0.02% pluronic acid (final concentrations) at 37° C. in 5% CO$_2$ for 30 min. The excess dye was removed by washing with assay buffer. The cells were resuspended and 10$^5$ cells/well were added in a Microlite plate containing compounds and then incubated for 15 minutes at 37° C. in 5% CO$_2$. The cells were then stimulated with MIP-1α and changes in intracellular free Ca$^{2+}$ concentration were measured with a Victor$^2$. The compounds of the invention, when tested in this assay, demonstrated the ability to inhibit the MIP-1α mediated Ca$^{2+}$ mobilisation in THP-1 cells.

In Vivo Bioavailability in the Mouse

Female mice (SJL/N Tac) were given a single intravenous or oral dose of a mixture of 5 or 6 compounds per cassette (nominal dose: 1 mg/kg/compound) in a solution containing 0.5% N,N'-dimethylacetamide (DMA) and 15% sulfobutyl ether β-cyclodextrin (Captisol®). Blood samples were taken from one mouse per time point and dose group until 24 hour after respective administration. The dose formulations and plasma concentrations of each compound were determined by LC-MS/MS. The pharmacokinetic parameters were determined by non-compartmental analysis using WinNonlin Professional (version 4.0.1). The elimination rate constant, λ, was estimated by linear regression analysis of the terminal slope of the logarithmic plasma concentration-time curve. The area under the plasma concentration-time curve, AUC$_{0-t}$, was calculated by using the linear/logarithmic trapezoidal rule. The AUC$_{inf}$ was calculated with the residual area estimated as C$_z$/λ. The calculated plasma concentration at the last time point, C$_z$, was obtained from the regression equation. The oral bioavailability (F) was calculated as:

$$F_{oral} = (AUC_{inf,po}/AUC_{inf,iv}) \cdot (Dose_{iv}/Dose_{po}).$$

Pharmacodynamic Assays

Using the procedures set forth in Horuk, R. and Ng, H. Med. Res. Rev. 2000, 20, 155 and Horuk, R. Methods, 2003, 29, 369 and references therein, the therapeutic efficacy of the compounds according to the invention for the treatment of inflammatory, autoimmune, proliferative or hyperproliferative diseases such as rheumatoid arthritis, multiple sclerosis, systemic lupus erythematosus, inflammatory bowel disease or asthma are shown.

Accordingly, in one embodiment of the invention a composition is provided comprising the compounds of formula I for the treatment of inflammatory, autoimmune, proliferative or hyperproliferative diseases.

The synergistic effect of combining the compounds according to the invention and cyclosporin A also is shown by use of methods mentioned in said references. Accordingly, in one embodiment of the invention a composition is provided comprising the compounds of formula I in combination with a sub-nephrotoxic amount of cyclosporin A.

Using the procedures set forth in the competitive affinity binding assay and the $Ca^{2+}$-flux assay, various compounds of the invention were tested for their ability to block $Ca^{2+}$-flux ($IC_{50}^{Ca}$). The results of some examples and the Compounds A, B, C, and D are shown in Table 2 where all $IC_{50}$-values are given in nM (nano Molar). Table 2 exemplifies the invention without limiting the scope thereof.

TABLE 2

| Compound | Structure | $IC_{50}^{Ca}$ |
|---|---|---|
| Compound A Prior art | 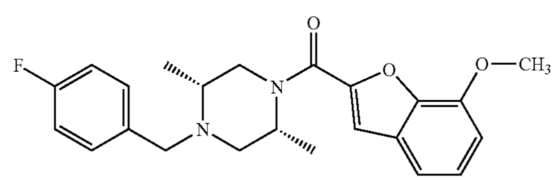 | >1000 |
| Compound D Reference | 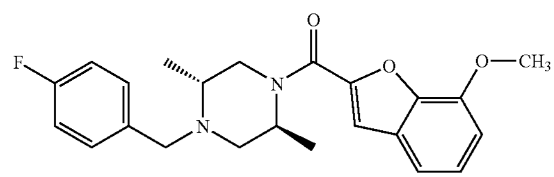 | >1000 |
| 3.1 Invention | 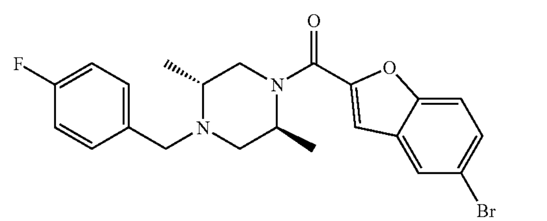 | 12 |
| 3.13 Invention | 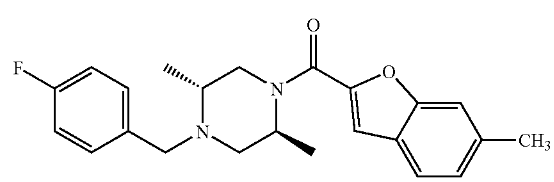 | 20 |
| Compound C Prior art | 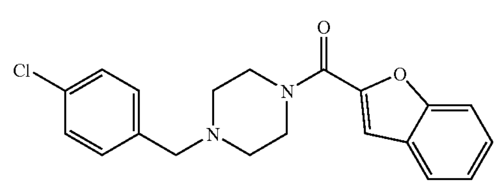 | >1000 |

TABLE 2-continued

| Compound | Structure | IC$_{50}$$^{Ca}$ |
|---|---|---|
| Compound B Reference | 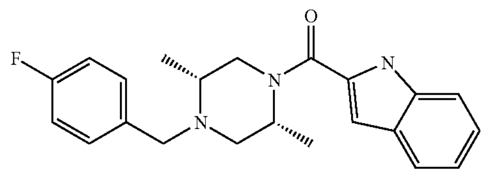 | >1000 |
| 3.20 Invention | 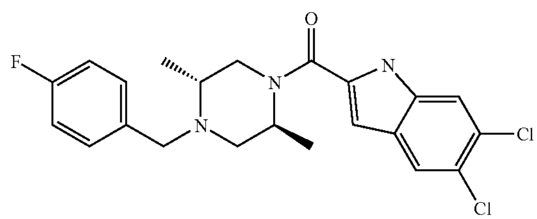 | 15 |

Footnote:
All 2,5-dimethylpiperazine derivatives have been synthesized and tested as racemic mixtures.

The compounds of the invention show oral bioavailability in the mouse. Using the procedures set forth in the in vivo bioavailability assay, various compounds of the invention were tested for their clearance (CL; L/h/kg), plasma half-life ($t_{1/2}$; hrs) as well as oral bioavailability (F; %) after administration of the nominal dose of 1 mg/kg of each compound. The results of some examples are shown in Table 3. Table 3 exemplifies the invention, without limiting the scope thereof.

mulated in usual pharmaceutical compositions comprising an effective amount of the active ingredient and suitable pharmaceutical constituents. Such compositions may take a variety of forms, e.g. solutions, suspensions, emulsions, tablets, capsules, and powders prepared for oral administration, sterile solutions for parental administration, suppositories for rectal administration or suitable topical formulations. Conventional procedures for the selection and preparation of suitable pharmaceutical formulations are

TABLE 3

| Compound | Structure | CL (L/h/kg) | $t_{1/2}$ (hrs) | F (%) |
|---|---|---|---|---|
| 3.1 | 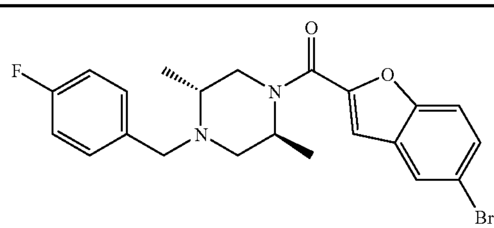 | 0.9 | 7.0 | 53 |
| 4.1 | 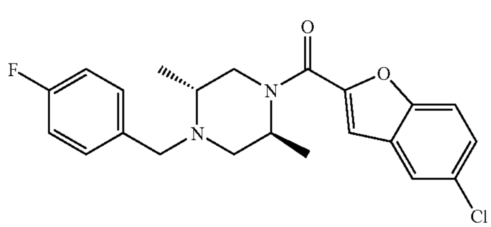 | 2.6 | 4.8 | 72 |

Administration

Effective quantities of the compounds of formula (I) are preferably administered to a patient in need of such treatment according to usual routes of administration and for-described, for example, in Pharmaceuticals—The Science of Dosage Form Design, M. B. Aulton, Churchill Livingstone, 1988.

A suitable daily dose for use in the treatment of RA is contemplated to vary between 0.005 mg/kg to about 10 mg/kg body weight, in particular between 0.025 mg/kg to 2 mg/kg bony weight, depending upon the specific condition to be treated, the age and weight of the specific patient and the specific patient's response to the medication. The exact individual dosage, as well as the daily dosage, will be determined according to standard medical principles under the direction of a physician.

The invention claimed is:

1. A compound of general formula (I)

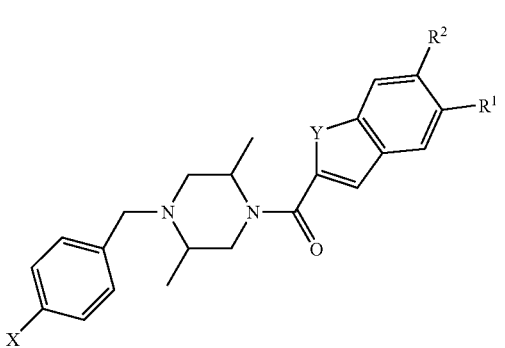

(I)

wherein:
X is a fluorine or a chlorine atom;
the methyl groups located at the 2- and 5-position of the piperazine ring are in trans-configuration to each other;
Y is O;
$R^1$ is hydrogen, chloro, bromo, nitro, methyl or trifluoromethyl;
$R^2$ is hydrogen, halo, methyl, trifluoromethyl, methoxy or trifluoromethoxy;
or a pharmaceutically acceptable salt.

2. A compound according to claim 1, wherein X is a fluorine atom;
Y is O;
$R^1$ is hydrogen, chloro or bromo;
$R^2$ is hydrogen, chloro, bromo, methyl, trifluoromethyl, methoxy or trifluoromethoxy.

3. A compound according to claim 1, selected from the group consisting of
(trans)-1-(5-Bromo-benzofuran-2-yl-carbonyl)-4-(4-fluorobenzyl)-2,5-dimethylpiperazine;
(trans)4-(4-Chlorobenzyl)-1-(5-chloro-indol-2-yl-carbonyl)-2,5-dimethylpiperazine;
(trans)-4-(4-Fluorobenzyl)-1-(6-methyl-benzofuran-2-yl-carbonyl)-2,5-dimethylpiperazine;
(trans)-4-(4-Fluorobenzyl)-1-(6-trifluoromethoxy-benzofuran-2-yl-carbonyl)-2,5-dimethylpiperazine;
(trans)-1-(5-Chloro-6-methoxy-benzofuran-2-yl-carbonyl)-4-(4-fluorobenzyl)-2,5-dimethylpiperazine;
(trans)-1-(5-Bromo-6-methoxy-benzofuran-2-yl-carbonyl)-4-(4-fluorobenzyl)-2,5-dimethylpiperazine;
(trans)-1-(5-Chloro-6-methyl-benzofuran-2-yl-carbonyl)-4-(4-fluorobenzyl)-2,5-dimethylpiperazine;
(trans)-1-(5-Bromo-6-methyl-benzofuran-2-yl-carbonyl)-4-(4-fluorobenzyl)-2,5-dimethylpiperazine;
(trans)-1-(5,6-Dichloro-indol-2-yl-carbonyl)-4-(4-fluorobenzyl)-2,5-dimethylpiperazine;
(trans)-1-(6-Bromo-5-chloro-indol-2-yl-carbonyl)-4-(4-fluorobenzyl)-2,5-dimethylpiperazine;
(trans)-1-(5-Bromo-6-chloro-indol-2-yl-carbonyl)-4-(4-fluorobenzyl)-2,5-dimethylpiperazine;
(trans)-1-(5-Chloro-6-trifluoromethyl-indol-2-yl-carbonyl)-4-(4-fluorobenzyl)-2,5-dimethylpiperazine; and
(trans)-1-(5-Chloro-benzofuran-2-yl-carbonyl)-4-(4-fluorobenzyl)-2,5-dimethylpiperazine.

* * * * *